(12) United States Patent
Gagnon et al.

(10) Patent No.: US 10,463,324 B2
(45) Date of Patent: Nov. 5, 2019

(54) PHOTON-COUNTING DETECTOR WITH COUNT-RATE DEPENDENT MULTIPLEXING

(71) Applicant: Toshiba Medical Systems Corporation, Otawara-shi (JP)

(72) Inventors: Daniel Gagnon, Twinsburg, OH (US); Gin Chung Wang, Lincolnshire, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 113 days.

(21) Appl. No.: 14/506,982

(22) Filed: Oct. 6, 2014

(65) Prior Publication Data
US 2016/0095559 A1    Apr. 7, 2016

(51) Int. Cl.
*A61B 6/03*    (2006.01)
*A61B 6/00*    (2006.01)
*G01T 1/17*    (2006.01)

(52) U.S. Cl.
CPC ............ *A61B 6/4241* (2013.01); *A61B 6/032* (2013.01); *A61B 6/4266* (2013.01); *A61B 6/482* (2013.01); *G01T 1/171* (2013.01)

(58) Field of Classification Search
CPC .............................. A61B 6/035; A61B 6/4241
See application file for complete search history.

(56) References Cited

U.S. PATENT DOCUMENTS

| | | | | |
|---|---|---|---|---|
| 6,061,132 A | * | 5/2000 | Girvin | G01N 15/0211 250/574 |
| 6,657,571 B2 | * | 12/2003 | Gordon | H03M 3/39 341/143 |
| 2007/0120062 A1 | | 5/2007 | Li et al. | |
| 2009/0121142 A1 | * | 5/2009 | Heismann | G01T 1/2018 250/363.04 |

(Continued)

FOREIGN PATENT DOCUMENTS

| | | |
|---|---|---|
| JP | 2000-131440 A | 5/2000 |
| JP | 2001-244814 A | 9/2001 |

(Continued)

OTHER PUBLICATIONS

Japanese Office Action dated Apr. 23, 2019 in Patent Application No. 2015-194565, 6 pages.

*Primary Examiner* — Mark D Remaly
(74) *Attorney, Agent, or Firm* — Oblon, McClelland, Maier & Neustadt, L.L.P.

(57) ABSTRACT

A photon-counting system includes photon-counting detectors that output photon-counting signals to indicate a number of photons impinging on the photon-counting detectors. The system also includes analog-to-digital conversion circuits, which convert one of the photon-counting signals into a digital photon-counting signals, and a processor that processes the digital photon-counting signals to extract information from the photon-counting signals. The information extracted can include a photon-counting rate. An intelligent multiplexer that, based on the photon-counting rate, modi- (Continued)

fies interconnection of the photon-counting detectors and analog-to-digital conversion circuits and provides digital photon-counting signals for a selected set of the analog-to-digital converters to the processor.

20 Claims, 7 Drawing Sheets

(56) References Cited

U.S. PATENT DOCUMENTS

| | | | |
|---|---|---|---|
| 2009/0309031 A1* | 12/2009 | Ohtani | G01T 1/2985 250/363.03 |
| 2013/0275054 A1* | 10/2013 | Simpson | G01J 1/16 702/26 |
| 2014/0110574 A1* | 4/2014 | Ugarov | H01J 49/40 250/252.1 |
| 2014/0197303 A1* | 7/2014 | Kelly | G11B 20/00086 250/208.1 |
| 2014/0233693 A1 | 8/2014 | Wang et al. | |

FOREIGN PATENT DOCUMENTS

| | | |
|---|---|---|
| JP | 2004-267402 A | 9/2004 |
| JP | 2009/78143 A | 4/2009 |
| JP | 2014-158714 A | 9/2014 |

\* cited by examiner

| Threshold | Detector-ADC Connection Pattern | ADC Output to Processor |
|---|---|---|
| TH1 | 1:1 | 1:1 |
| TH2 | 1:2 | 2:1 |
| TH3 | 1:4 | 4:1 |
| TH4 | 1:1 (Integration Mode) | 1:1 (Integration Mode) |

PHOTON-COUNTING DETECTOR WITH COUNT-RATE DEPENDENT MULTIPLEXING

FIELD

Embodiments described herein generally relate to photon-counting detectors used in, for example, computer-aided tomography (CT) systems.

BACKGROUND

CT systems are widely used in medical and industrial applications. These systems often include photon-counting detectors that are able to count individual photons that impinge on them and generate a corresponding signal. However, the signals from photon-counting detectors must be digitized before they can be processed into usable data, such as images.

Conventionally, the signals from the photon-counting detectors are provided to analog-to-digital converters (ADC) for digitizing. However, conventional ADCs limit CT system performance and resolution by the amount of time required to perform an analog-to-digital conversion. Although, high-speed ADCs exist, such high-speed ADCs are often prohibitively expensive. Thus, the ADCs used in CT systems remain a bottleneck to system performance, cost or both.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

In certain applications, mid-speed, low-resolution ADCs may be used to digitize signals from photon-counting detectors. The photon-counting detectors and ADCs may be arranged (multiplexed) based on the current photon-counting rate to yield high sampling rates despite the fact that the ADCs are not high-speed.

According to one exemplary embodiment of the present disclosure, a photon-counting apparatus includes multiple photon-counting detectors that generate photon-counting signals by counting the number of photons impinging on the photon-counting detectors. The apparatus also including multiple analog-to-digital conversion circuits, each of which converts a respective one of the photon-counting signals into a digital photon-counting signal. A processor that processes the digital photon-counting signals to extract information from them extracts a photon-counting rate, and an intelligent multiplexer modifies interconnections between the photon-counting detectors and the analog-to-digital conversion circuits based on the photon-counting rate. The intelligent multiplexer also provides a selected set of digital photon-counting signals to the processor.

In the exemplary embodiment, the intelligent multiplexer interleaves digital photon-counting signals of a subset of analog-to-digital conversion circuits when the photon-counting rate exceeds a first threshold, where the subset of analog-to-digital conversion circuits may be two analog-to-digital conversion circuits.

In the exemplary embodiment, the intelligent multiplexer interleaves the photon-counting signals of three analog-to-digital conversion circuits when the photon-counting rate exceed a second threshold that is higher than the first threshold.

In the exemplary embodiment, the intelligent multiplexer interleaves the photon-counting signals of four analog-to-digital conversion circuits when the photon-counting rate exceeds a third threshold that is higher than the second threshold.

In the exemplary embodiment, the analog-to-digital conversion circuits switch to an integration mode in which they use oversampling and decimation to generate the digital photon-counting signals when the photon-counting rate exceeds a fourth threshold that is higher than the third threshold. The intelligent multiplexer then provides all of the digital photon-counting signals to the processor.

In the exemplary embodiment, the photon-counting apparatus also includes an energy integrating detector that integrates signals from photon-counting detectors adjacent to the plurality of photon-counting detectors in order to determine the photon-counting rate.

In the exemplary embodiment, the photon-counting apparatus also includes additional photon-counting detectors distributed among the photon-counting detectors to provide an indication of the photon-counting rate.

In the exemplary embodiment, the photon-counting apparatus also includes a preamplifier circuit to condition the photon-counting signals from the photon-counting detectors, and during an auto-adjust phase during with the preamplifier circuit is adjusted, the processor uses the initial waveforms of the digital photon-counting signals to determine the photon-counting rate. For example, the processor may use a difference between levels of the digital photon-counting signals and a predetermined base line level.

In the exemplary embodiment, the intelligent multiplexer may be implemented in a Field Programmable Gate Array (FPGA) or a processor, such as a digital signal processor (DSP). The processor of the photon-counting apparatus may also be a DSP or a general purpose processor.

In the exemplary embodiment, the photon-counting apparatus may also include an electronic memory circuit to store a look-up table that associates different interconnection patterns between the photon-counting detectors and analog-to-digital conversion circuits with the first-fourth thresholds, and associates different interleaving patterns of the digital photon-counting signals from the analog-to-digital conversion circuits with the first-fourth thresholds.

In the exemplary embodiment, the photon-counting apparatus may also be included in a computer-aided tomography (CT) system to capture data from the photon-counting detectors.

In the exemplary embodiment, the CT system includes an X-ray tube to generate the photons that impinge on the photon-counting tubed and a reconstruction circuit that reconstructs CT images based on the digital photon-counting signals generated by the intelligent multiplexer.

In the exemplary embodiment, the X-ray tube rotates around a patient table, and the photon-counting detectors are located at fixed positions around the patient table.

In the exemplary embodiment, the photon-counting rate is a number of photons impinging on the photon-counting detectors during a predetermined time interval.

In another exemplary embodiment of the present disclosure, a method for a photon-counting apparatus includes generating a plurality of photon-counting signals based on impingement of photons on a plurality of photon-counting detectors, and converting at least a subset of the plurality of photon-counting signals to digital photon-counting signals in a plurality of analog-to-digital conversion circuits. The method also includes determining a photon count rate in a processor, and causing an intelligent multiplexer to modify interconnections between the plurality of photon-counting detectors and the plurality of analog-to-digital conversion circuits based on the photon count rate, where the intelligent multiplexer also provides a selected set of digital photon-counting signals to the processor.

In a further exemplary embodiment of the present disclosure, a non-transitory computer-readable medium encoded with computer-readable instructions thereon that, when executed by a computer, cause the computer to perform a method that includes generating a plurality of photon-counting signals based on impingement of photons on a plurality of photon-counting detectors. The method also includes converting at least a subset of the plurality of photon-counting signals to digital photon-counting signals in a plurality of analog-to-digital conversion circuits, and determining a photon count rate in a processor. Then an intelligent multiplexer is caused to modify interconnections between the plurality of photon-counting detectors and the plurality of analog-to-digital conversion circuits based on the photon count rate, and to provide a selected set of digital photon-counting signals to the processor.

Figure 1:
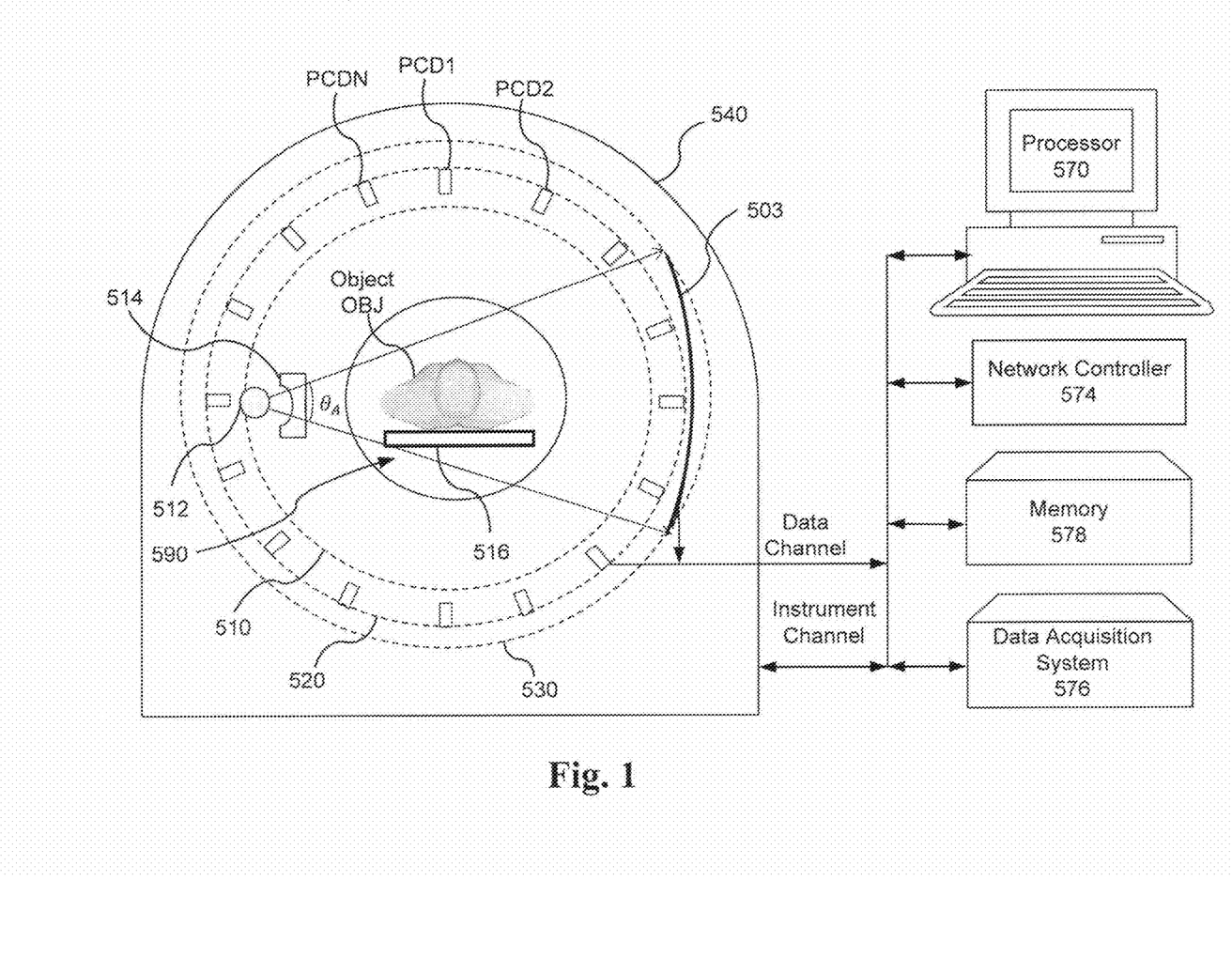
FIG. 1 is a schematic of a CT system according to exemplary aspects of the present disclosure.

Referring now to the drawings, wherein like reference numerals designate identical or corresponding parts throughout the several views. FIG. 1 illustrates a CT system that includes photon counting detectors PCD1, PCD2, . . . PCDn positioned around an object OBJ to be scanned, such as a patient. The object to be scanned OBJ rests on a patient table 516 and is irradiated by an X-ray source 512, such as an X-ray tube, via a collimator/filter 514. A third generation detector unit 503 may also be included, and the photon-counting detectors may be part of a fourth generation geometry, but other geometries are possible without departing from the scope of the present disclosure.

The photon-counting detectors have a front surface oriented towards the object to be scanned OBJ and a back surface oriented away from the object to be scanned. X-rays traveling through the object OBJ are either detected by the photon-counting detectors PCD1-PCDn (at the front surface) or pass through space between the photon-counting detectors PCD1-PCDn and are detected by the third generation detector unit 503. Further the X-ray source 512, collimator/filter and detector unit 503 rotate about the object OBJ and the patient table 516, but the photon-counting detectors PCD1-PCDn remain at a fixed position relative to the patient table 516.

Also shown in FIG. 5 is circuitry for acquiring, storing, processing and distributing X-ray projection data. The circuitry may include hardware such as a processor 570, a network controller 574, a memory 578, and a data acquisition system 576. The photon-counting system according to exemplary aspects of the present disclosure may form part of the data acquisition system 576 and includes the photon-counting detectors PCD1-PCDn. In one exemplary aspect, the X-ray source 512 and the collimator/filter 514 are fixedly connected to a first rotational component 510 that is rotatably connected to the gantry 540. The X-ray detector 503 is similarly fixedly connected to a second rotational component 530 that is rotatably connected to the gantry 540. As noted above, the photon-counting detectors PCD1-PCDn are fixedly connected to a circular component 520 that is fixedly connected to the gantry 540. The gantry 540 houses many, and in some cases all, of the components of the CT system.

The gantry of the CT system also includes an open aperture 590 that enables the object OBJ to be disposed on the patient table 516 that is positioned in a projection plane of the X-rays traveling from the X-ray source 512 to the photon-counting detectors PCD1-PCDn. The projection plane is a volume in which X-rays pass from the X-ray source 512 to the photon-counting detectors PCD1-PCDn. A scan is performed when the object OBJ is on the patient table 516 and the X-ray source 512 is rotated through a series of projection angles with the CT system acquiring projection data of the X-ray transmission/attenuation through the object OBJ at each projection angle.

As is described in greater detail below, X-ray transmission/attenuation through the object OBJ is captured by the photon-counting detectors PCD1-PCDn as individual photons impinge thereon. The data acquisition system 576 includes the necessary circuitry, such as filter circuits, analog-to-digital conversion circuits, multiplexers and processors, such as a digital signal processor, to process the signals generated by the photon-counting detectors PCD1-PCDn and to the processed signals to the processor 570 for reconstruction of a CT image based on the acquired data from the photon-counting detectors. In this sense, the processor 570 may be considered a reconstruction circuit which includes the necessary circuit to process and reconstruct CT images. Image processing techniques are employed by the processor 570 in order to reconstruct the CT images from the digital signals provided to it by the data acquisition system 576 and which are based on the signals from the photon-counting detectors PCD1-PCDn. In FIG. 1, the data acquisition system 576 is located outside of the gantry 540, and connects with instrument channel. But the data acquisition system 576 can be integrated inside of the gantry 540.

The circuitry of the processor 570 may include a processing circuit, such as a microprocessor, microcontroller or digital signal processor that runs an operating system, such as Linux, Unix, Windows or Mac OS. However, these circuits may also be implemented in a field programmable gate array (FPGA), complex programmable logic device (CPLD), programmable logic device (PLD) or individual logic gates. The circuitry may also be implemented as an application specific integrated circuit (ASIC). Of course, the processor 570 may also include random access memory (RAM), read only memory (ROM), or erasable read only memory (EPROM) to store computer readable instruction and other data necessary for reconstruction of the CT images, as one of ordinary skill would recognize. Therefore, further descriptions of the ancillary circuitry of the processor 570 is omitted for brevity.

Returning to FIG. 1, the photon-counting detectors PCD1-PCDn may be sparsely located about the patient table 516, or may be more densely packed about the patient table. The collimator/filter 514 may be a "bow-tie" filter, for example. Also, the X-ray source 512 may travel a helical path about the object OBJ and patient table 516. As such, the above descriptions are exemplary and in no way limit the present disclosure.

Figure 2:
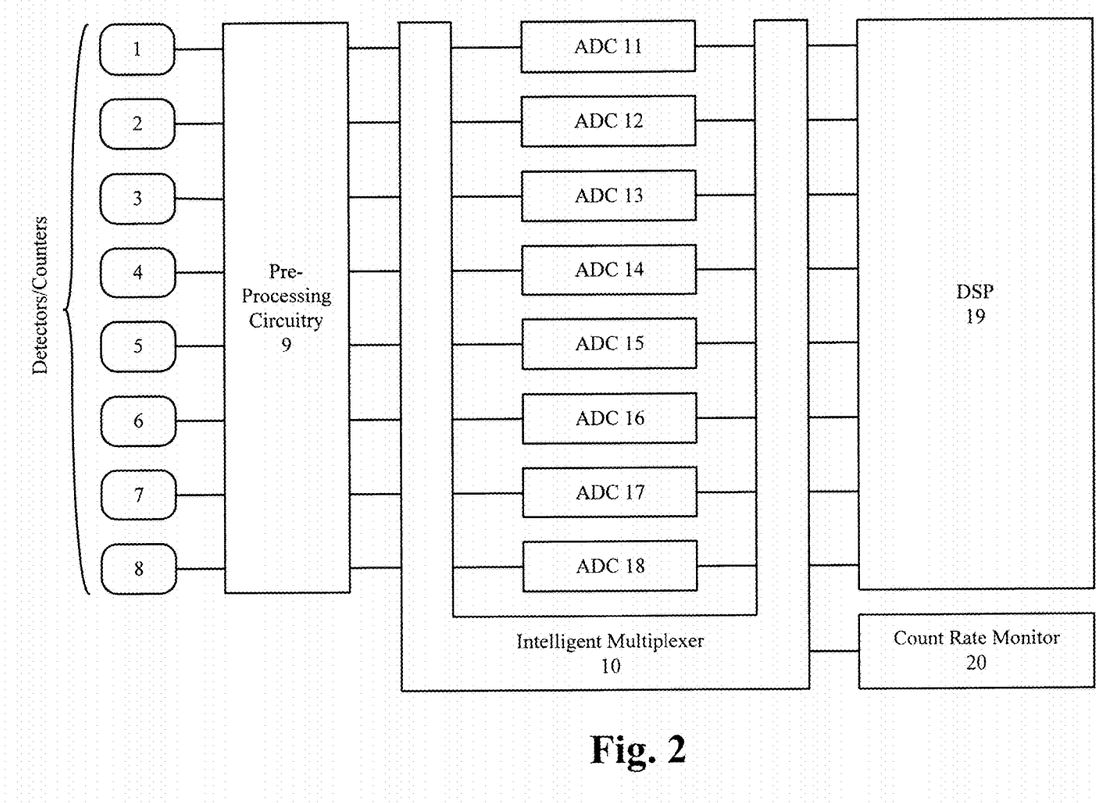
FIG. 2 is a schematic of a photon-counting system according to exemplary aspects of the present disclosure.

FIG. 2 is a schematic of a photon-counting system according to exemplary aspects of the present disclosure. As noted above, this photon counting system may be implemented in the data acquisition system 576 of FIG. 1, for example. In FIG. 2 photon-counting detectors 1-8 are connected to preprocessing circuitry 9, which is in turn connected to the intelligent multiplexer 10. The intelligent multiplexer 10 is then connected to the analog-to-digital conversion (ADC) circuits 11-18. The intelligent multiplexer 10 is connected to both inputs and outputs of the ADC circuits 11-18 in order to control both the signals provided to the ADC circuits 11-18 and the provision of the output signals of the ADC circuits 11-18 to other devices such as digital signal processor (DSP) 19.

As noted above, the intelligent multiplexer 10 is also connected to a processor, such as DSP 19, which processes the signals digitized by the ADC circuits 11-18. A count rate monitor 20 is also connected to the intelligent multiplexer 10, since the intelligent multiplexer changes the connections between the photon-counting detectors 1-8 and the ADC circuits 11-18 and between the ADC circuits 11-18 and the DSP 19.

The photon-counting detectors 1-8 may be photomultipliers, single-photon avalanche diodes, superconducting nanowire single-photon detectors, transition edge sensors or scintillation counters. The photon-counting detectors 1-8 generate an electronic signal when impinged upon by individual photons, making photon-counting possible. Thus, any device capable of generating a signal indicative of the number of photons impinging upon it can be used without departing from the scope of the present disclosure.

The preprocessing circuitry 9 can include analog amplifiers, filters and equalizers that are used to condition the signals generated by the photon-counting detectors 1-8. The amplifiers, filters and equalizers may be constructed using discrete components, such as transistors, capacitors, diodes, resistors, inductors, etc., or may be ready-made devices in the form of integrated circuits. The preprocessing circuitry 9 may also be integrated into a single chip, such as an Application Specific Integrated Circuit (ASIC) or a Field Programmable Analog Array (FPAA).

The ADC circuits 11-18 take the analog signals that originate from the photon-counting detectors 1-8 and that are conditioned by the preprocessing circuitry 9, and digitize them to generate digital signals indicative of the number of photons impinging on the photon-counting detectors 1-8. As such, the ADC circuits 11-18 may be implemented as separate, discrete devices using transistors, diodes and passive electronic components, or may be implemented together in an ASIC, FPAA or other single-chip device. The ADC circuits 11-18 may perform their conversion directly using a bank of comparators (direct-conversion ADC) or may use a single comparator to successively narrow a range that contains the target voltage (successive-approximation ADC). Other ADC circuit types, such as Wilkinson ADCs, integrating ADCs—both dual slope and multi-slope—delta-encoded ADCs, pipeline ADCs and sigma-delta ADCs are also possible.

The intelligent multiplexer 10 determines the connections between the photon-counting detectors 1-8 and the ADC circuits 11-18 as will be described in greater detail below. As such, the intelligent multiplexer may be implemented using discrete logic devices, an ASIC or a Field Programmable Gate Array (FPGA). The intelligent multiplexer 10 may also be implemented as code executed by a general purpose processor or a digital signal processor. Such general purpose processor or digital signal processor may, in turn, be implemented in a logic device, such as an FPGA.

The DSP 19 of FIG. 2 processes the digitized signals generated by the ADC circuits 11-18 to extract information from those signals, such as a photon count rate. Though FIG. 2 illustrates the processor as a digital signal processor, DSP 19, DSP 19 may instead be a general purpose processor. Either DSP or general purpose processors having Von Neumann architecture, Harvard architecture, Super Harvard architecture, or a reduced instructions set architecture (RISC), such as ARM. DSP 19 may also be implemented in an FPGA or an ASIC. If the DSP 19 is implemented in an FPGA or ASIC, it may be combined with the intelligent multiplexer 10 such that both devices are on a single chip.

Regardless of implementation, the DSP 19 may control all of the functions of the photon-counting system though the execution of code. Such code may be stored in an electronic memory (not shown), such as random access memory (RAM), read only memory (ROM), FLASH memory, electrically erasable read only memory (EEPROM) and the like. The electronic memory may be integrated into the same chip as the DSP 19 or may be a separate device that is connected to the DSP 19 via, for example, a printed circuit board. At least part of the memory may be removable. The DSP 19 may also execute the code using an operating system, such as UNIX, LINUX, Windows, Android or IOS, or may execute the code directly without an intervening operating system. Numerous other variations are also possible without departing from the scope of the present invention.

Also connected to the intelligent multiplexer 10, is a count rate monitor 20 which determines the photon count rate that is used by the intelligent multiplexer to control the ADC circuits' 11-18 connections. For example, the count rate monitor 20 may use photon-counting detectors adjacent to the photon-counting detectors 1-8 in order to estimate the photon-counting rate through energy integration. The count rate monitor 20 may also use additional reference detectors that are distributing in the array of photon-counting detectors in order to estimate the photon-counting rate, again through energy integration. The count rate monitor 20 may also use the initial wave forms generated by the ADC circuits 11-18, or that are output by the preprocessing circuitry 9, to estimate the photon-counting rate. For example, during auto-adjustment, the preprocessing circuits level may be shifted up from a baseline—for example zero volts—by a certain amount. This up shift in the level of the preprocessing circuit 9 relative to the baseline level may be used as a good estimate of the photon-counting rate. Other techniques to determine the photon-counting rate are also possible without departing from the scope of the present disclosure.

As can be appreciated, the count rate monitor 20 may be implemented using discrete components, such as amplifiers, logic gates, transistors, passive elements, etc., or may be implemented in an ASIC or FPGA. The count rate monitor 20 may also be implemented in code in, for example, the DSP 19. The count rate monitor 20 may even be integrated into the intelligent multiplexer 10 or the DSP 19, for example in an ASIC or FPGA or a processor, in a system on a chip (SOC) implementation. Of course, the photon-counting system of FIG. 2 includes other components for power distribution, circuit protection and communication, bot wired and wireless (i.e., USB, Ethernet, WiFi, Bluetooth, etc.) However, as these components are known they are neither illustrated in FIG. 2 nor discussed further for the sake of brevity.

Figure 3:
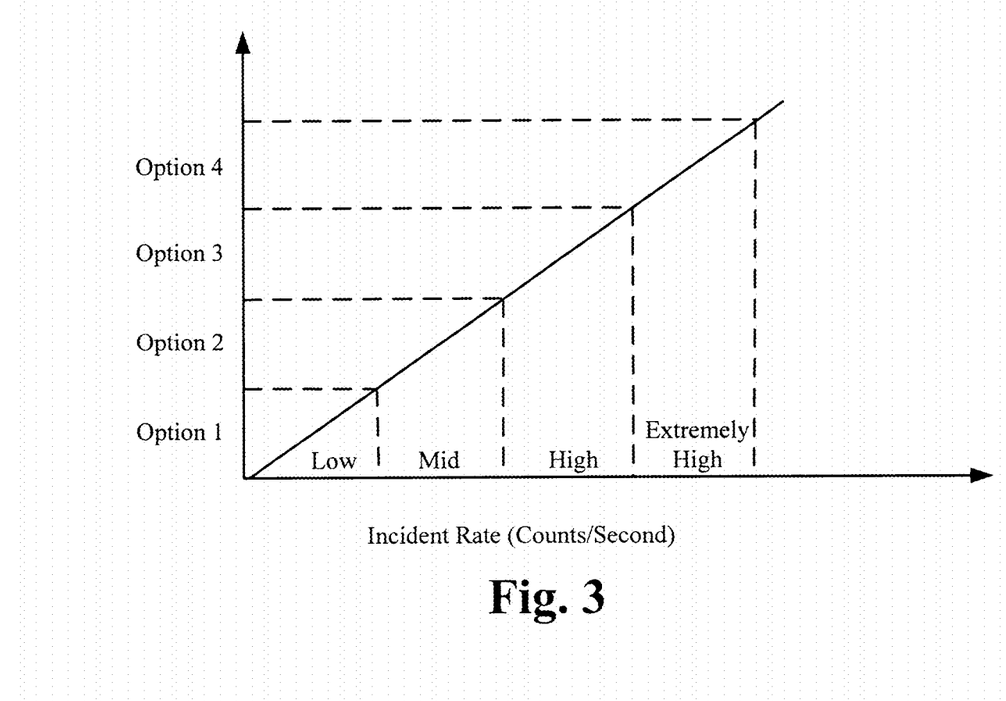
FIG. 3 is a graph of the relationship between multiplexing options and photon-counting rates according to exemplary aspects of the present disclosure.

FIG. 3 is a graph of the control function used by the intelligent multiplexer 10 in determining how to connect the photon-counting detectors 1-8 to the ADC circuits 11-18 and the ADC circuits 11-18 to the DSP 19. In FIG. 3, the vertical axis represents the number of options, or connection patterns, that the intelligent multiplexer 10 uses to make the different connections, and the horizontal axis represents the photon-counting rate in counts per second. The photon-counting rate increases with distance from the vertex at which the vertical and horizontal axes meet. Though four options are shown for the sake of brevity, one of ordinary skill in the art will recognize that the number of options can be greater or less than four, such that the four options illustrated are exemplary and do not limit the present disclosure.

When the counting rate is low, the intelligent multiplexer 10 may establish the first option, option 1, which is illustrated in FIG. 2, for example. In option 1, each photon-counting detector 1-8 is connected via the intelligent multiplexer 10 to one of the ADC circuits 11-18 such that there is a 1:1 correspondence between the photon-counting detectors and the ADC circuits 11-18. For example, photon-counting detector 1 is connected to ADC circuit 11, photon-counting detector 2 is connected to ADC circuit 12, photon-counting detector 3 is connected to ADC circuit 13 and so on. Even though the ADC circuits 11-18 may not be high-speed circuits, because the number of counts per second (i.e., the counting rate) is low, they are still able to perform analog-to-digital conversions at a rate that yields sufficient resolution to reliably count individual photons.

When the photon count rate is in the middle range, "Mid" in FIG. 3, the ADC circuits 11-18 may not be able to perform their conversions fast enough to have the proper resolution. Therefore, the intelligent multiplexer 10 reconfigures the connections among the photon-counting detectors 1-8, the ADC circuits 11-18 and the DSP 19 according to option 2.

Figure 5:
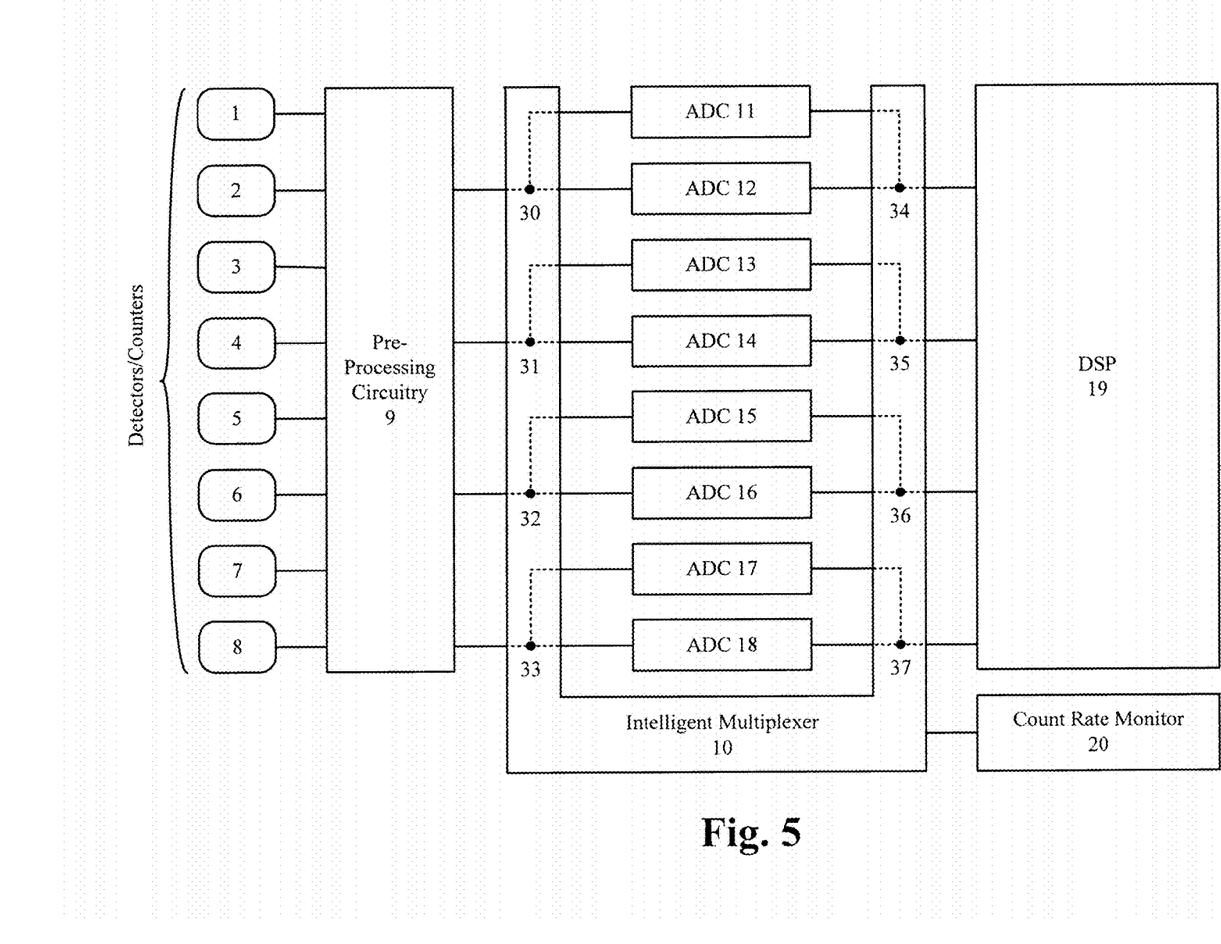
FIG. 5 is a schematic of a multiplexing option according to exemplary aspects of the present disclosure.

As shown in FIG. 5, in option 2, every other photon-counting detector is skipped so that photon-counting detectors 1, 3, 5 and 7 are not connected to the ADC circuits 11-18. They can, however, continue to be used to estimate the photon-counting rate as described above with respect to the count rate monitor 20. The other photon-counting detectors 2, 4, 6 and 8 are connected to the ADC circuits 11-18 in a 1:2 ratio. That is, photon-counting detector 2 is connected to both ADC circuits 11-12 via connection 30, photon-counting detector 4 is connected to both ADC circuits 13-14 via connection 31, photon-counting detector 6 is connected to both ADC circuits 15-16 via connection 32, and photon-counting detector 8 is connected to both ADC circuits 17-18 via connection 33. The multiplexer also interleaves the outputs of the ADC circuits connected to a particular photon-counting detector and provides the result to the DSP 19 through a reduced set of connections. For example, the outputs of ADC circuits 11-12 are interleaved and provided to the DSP 19 via connection 34, the outputs of ADC circuits 13-14 are interleaved and provided to the DSP 19 via connection 35, the outputs of ADC circuits 15-16 are interleaved and provided to the DSP 19 via connection 36, and the outputs of ADC circuits 17-18 are interleaved and provided to the DSP 19 via connection 37. By using two ADC circuits for every one detector and interleaving the outputs of the two ADC circuits, the intelligent multiplexer can effectively reduce the conversion time of the signals from the photon-counting detectors 2, 4, 6 and 8 and maintain a resolution that allows for reliable photon-counting.

Figure 6:
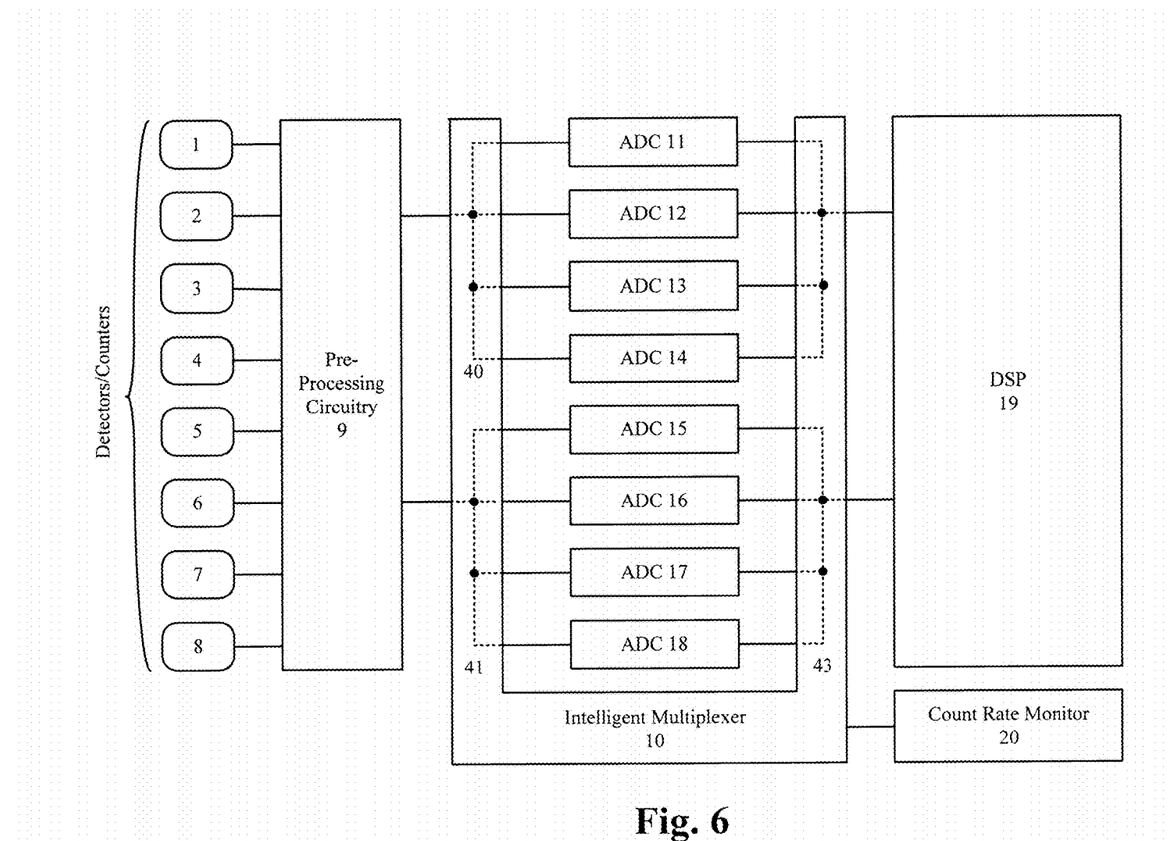
FIG. 6 is a schematic of another multiplexing option according to exemplary aspects of the present disclosure.

Returning to FIG. 3, when the photon-counting rate is in the "high" range, the intelligent multiplexer changes the connections among the photon-counting detectors 1-8, the ADC circuits 11-18 and the DSP 19 to option 3. As shown in FIG. 6, the intelligent multiplexer 10 organizes the ADC circuits 11-18 into groups of four and connects each group of ADC circuits to a single photon-counting detector. In FIG. 6 ADC circuits 11-14 are connected to photon-counting detector 2 via the connection 40 in the intelligent multiplexer 10. ADC circuits 15-18 are connected to photon-counting detector 6 via connection 41 of the intelligent multiplexer 10. Photon-counting detectors 1, 3-5 and 7-8 are not used, but remain available for photon-counting rate determination by the counting rate monitor 20, as described above.

The intelligent multiplexer 10 interleaves the outputs of ADC circuits 11-14 and provides the interleaved signal to the DSP 19 via the connection 42. The intelligent multiplexer 10 also interleaves the outputs of ADC circuits 15-18 and provides the interleaved output to the DSP 19 via connection 43. In this way the intelligent multiplexer 10 is able to effectively decrease the conversion time of the signals from the photon-counting detectors 2 and 6 such that ADC circuits 11-14 as a group and ADC circuits 15-18 as a group provide the necessary resolution to digitize the photon-counting detector signals resulting from higher photon count rates.

In options 2 and 3 the intelligent multiplexer interleaves the outputs of two or more ADC circuits 11-18 in order to provide an interleaved signal to the DSP 19. One example of interleaving is time-multiplexing the signals from the ADC circuits such that each is allotted a timeslot in the overall interleaved signal. For example, in the case of interleaving ADC circuits 11 and 12, samples may be alternated in time so that a sample from ADC circuit 11 precedes a sample from ADC circuit 12 and the cycle repeats. Of course, a sample of ADC circuit 12 can also precede a sample of ADC circuit 11, such that the exact order of the interleaving is not limiting on the present disclosure. Though FIGS. 5 and 6 show that the interleaved signals are provided to the DSP 19 via a single connection, each ADC circuit 11-18 may maintain its connection to the DSP 19 and deliver its samples to the DSP 19 via that connection. The intelligent multiplexer 10 may then stagger the samples of the ADC circuits 11-18 using delay lines or other known methods in order to achieve the time-interleaving discussed above (i.e., a sample of ADC circuit 11 arrives at the DSP 19 before a sample of the ADC circuit 12). Other interleaving schemes are also possible as one of ordinary skill would recognize.

Also, in FIGS. 5 and 6 the ADC circuits 11-18 are connected to the photon-counting detectors in groups of 2 and 4 respectively. However, other combinations are also possible. For example three of the ADC circuits 11-18 may be assigned to one photon-counting detector or more than four ADC circuits 11-18 may be assigned to a single photon-counting detector. Further, though only eight photon-counting detectors 1-8 and eight ADC circuits 11-18 are shown for simplicity, greater numbers of photon-counting detectors and ADC circuits may be used without departing from the scope of the present disclosure.

Returning to FIG. 3, when the photon-counting rate is in the extremely high range, interleaving of the ADC circuits 11-18 may not be sufficient to provide adequate resolution. In this case the intelligent multiplexer may also instruct the ADC circuits 11-18 to switch to an integration mode in order to provide the required resolution for photon-counting at the extremely high rate. In the integration mode, the ADC circuits 11-18 oversample the signals from the photon-counting detectors 1-8, after conditioning by the preprocessing circuitry 9, in order to obtain the required resolution, perform the conversion and then decimate the converted, i.e., digitized, signal after the conversion. In option 4, each photon-counting detector 1-8 is connected to an ADC circuit 11-18 in a 1:1 correspondence by the intelligent multiplexer 10. The intelligent multiplexer also provides the outputs of all ADC circuits 11-18 to the DSP 19.

Of course, though only 4 options are shown in FIG. 3, many other options are possible. For example, the ADC circuits may be placed in the integration mode, and may be grouped as in options 2 and 3 in order to provide better resolution at higher photon-counting rates. Also, in the event that more than one ADC circuit 11-18 is connected to a single photon-counting detector, only a subset of this group of detectors can be placed in the integration mode. Thus, aspects of the different embodiments and options described above can be freely combined without limitation, and as such are not limiting upon the present disclosure.

As described above, aspects of this disclosure may be implemented as software executing on a processor. In order to implement the different modes according to photon count rate, a look up table such as the one of FIG. 4 may be stored in internal memory of the processor, on memory external to the processor or even on removable memory to allow for modification and updates of the different options included in the look up table.

Figure 4:
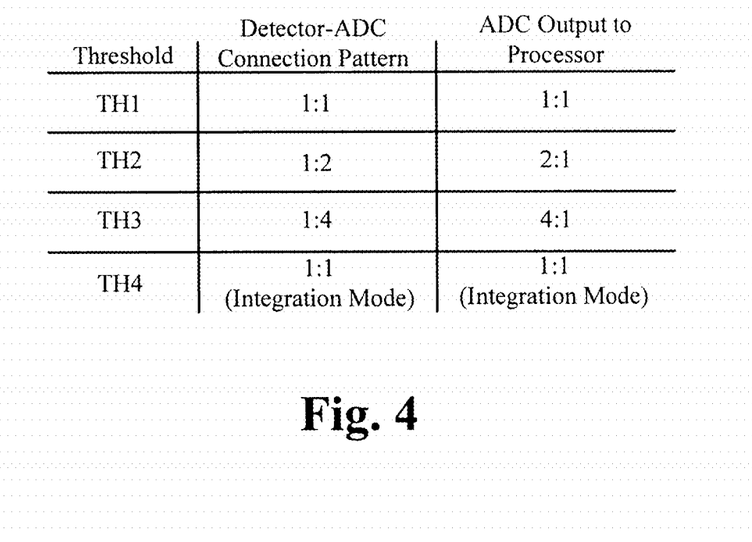
FIG. 4 is a look-up table associating counting rate thresholds to multiplexing options according to exemplary aspects of the present disclosure.

In FIG. 4, the leftmost column entitled "Threshold" is used as a table index and corresponds to the photon-counting rates that form the boundaries between the different options. Thus, if the photon-counting rate exceeds a threshold, the system will shift to the next option. Each of the values in the "Threshold" column, TH1, TH2, TH3, TH4 are variables that can be adjusted based on the performance characteristics of the ADC circuits 11-18 used. The "Detector-ADC Connection Pattern" identifies how the ADC circuits 11-18 are to be connected to the detectors. For example, if the pattern is 1:1, then each photon-counting detector 1-8 will be connected to its one ADC circuit 11-18. If the connection pattern is 1:2, then each photon-counting detector 1-8 will be connected to two ADC circuits 11-18, and so on. Of course, instead or in addition to the connection pattern, the look up table of FIG. 4 may expressly identify which photon-counting detectors 1-8 are to be connected to which ADC circuits 11-18 without departing from the scope of the present advancements.

The column entitled "ADC Output to Processor" defines the interconnection between the ADC circuits 11-18 and the input pins of the processor (DSP 19). For example, if there is a 1:1 correspondence, then each ADC circuit 11-18 is connected to a separate input pin of the processor. If there is a 2:1 correspondence then two ADC circuit outputs are interleaved into a single input pin of the processor, and so on. As is the case with the connections between the photon-counting detectors 1-8 and the ADC circuits 11-18, the interconnections between the ADC circuit outputs and the input pins of the processor may be expressly defined for each option in the look up table.

Figure 7:
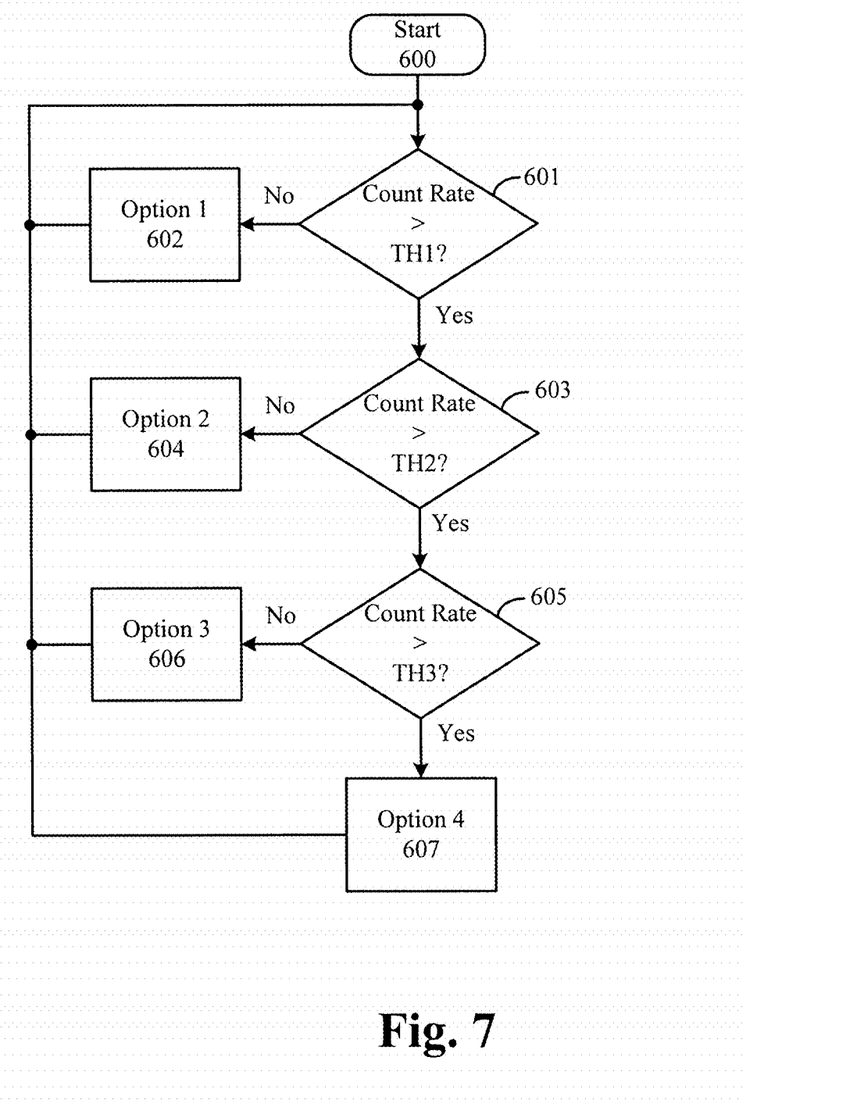
FIG. 7 is an algorithmic flowchart of multiplexing option selection according to exemplary aspects of the present disclosure.

Next, selection of the different options in the look up table of FIG. 3 is described with reference to the algorithmic flowchart of FIG. 7. In FIG. 7, the process begins at step 600 and proceeds to step 601 where the current photon count rate is compared to the first threshold in the look up table of FIG. 4. If the current photon count rate is equal to or less than the threshold TH1, then the system selects, or remains, in option 1 at step 602. As discussed above, option 1 is where each photon-counting detector 1-8 is connected to a single, separate ADC circuit 11-18. Once in option 1, the system reverts to step 600 to again compare the photon-counting rate with the different thresholds TH1, TH2, TH3 as the photon-counting rate changes.

If at step 601 the current photon-counting rate exceeds the threshold TH1, the process proceeds to step 603 to compare the current photon-counting rate with threshold TH2. If the current counting rate does not exceed TH2, the process proceeds to step 604 to enter, or remain in, option 2. As noted above, in option 2 the ADC circuits 11-18 are grouped in pair with each pair connected to every other of photon-counting detectors 1-8. The process then reverts to step 600 to compare another photon-counting rate value with the thresholds TH1, TH2 and TH3.

If at step 603, the threshold TH2 is exceeded, the process moves to step 605 to compare the photon-counting rate with the threshold TH3. If the photon-counting rate is below the TH3, the process moves to step 606 to enter or remain in option 3, which is the option where the ADC circuits 11-18 are grouped in groups of 4 that are connected to every third of photon-counting detectors 1-8. The process then reverts to step 600 to compare another photon-counting rate value with the thresholds TH1, TH2 and TH3.

If the photon-counting rate exceeds TH3, the process moves to step 607 in order to enter or remain in option 4. As described above, in this option each photon-counting detector 1-8 is connected to a separate ADC circuit 11-18, but the ADC circuits are placed in the integration mode to better resolution. Also, note that it is not necessary to compare the photon-counting rate with TH4 since option 4 is the last option, and the process checks each threshold beginning with TH1. If, however, the process checked thresholds beginning with TH4 and working down towards TH1, the checking of TH1 would not be necessary since it is the last of the thresholds.

Though the algorithmic process of FIG. 4 has been described as a continuous loop, other structures are possible. For example, the process may compare the current count rate in parallel and determine which option to use based on the outcomes of the comparison. The process also need not execute continuously. Instead, the process may be interrupt-driven and only execute when the value of the photon-counting rate changes, or when the value of the photon-counting rate exceeds the threshold TH1-TH4 corresponding to the current option being used. A user override may also be provided to lock the system in one of the options regardless of the photon-counting rate.

Any processes, descriptions or blocks in flowcharts should be understood as representing modules, segments, portions of code which include one or more executable instructions for implementing specific logical functions or steps in the algorithmic process, and alternate implementations are included within the scope of the exemplary aspects of the present disclosure in which functions may be executed out of order from that shown or discussed, including substantially concurrently or in reverse order, depending upon the functionality involved, as would be understood by those skilled in the art. Further, it is understood that any of these processes may be implemented as computer-readable instructions stored on computer-readable media, such as electronic memory circuits, magnetic storage media, optical storage media and the like, for execution by a processor.

Obviously, numerous modifications and variations of the present invention are possible in light of the above teachings. It is therefore to be understood that within the scope of the appended claims, the invention may be practiced otherwise than as specifically described herein.

The invention claimed is:

1. A photon-counting apparatus, comprising:
a plurality of first photon-counting detectors configured to output photon-counting signals indicative of a number of photons impinging on the first photon-counting detectors;
a plurality of analog-to-digital conversion circuits, each configured to convert a respective one of the photon-counting signals into a digital photon-counting signal;
a processor configured to process the digital photon-counting signals to extract information from the digital photon-counting signals, the information including a photon-counting rate; and
an intelligent multiplexer including a first portion configured to form connections from outputs of the first plurality of photon-counting detectors to inputs of the plurality of analog-to-digital conversion circuits and a second portion configured to form connections from outputs of the plurality of analog-to-digital conversion circuits to inputs of the processor, the intelligent multiplexer being configured to, based on the photon-counting rate, modify the connections from the outputs of the first plurality of photon-counting detectors to the inputs of the plurality of analog-to-digital conversion circuits and to provide digital photon-counting signals for a set of the plurality of analog-to-digital converters to the processor based on the connections from the outputs of the plurality of analog-to-digital conversion circuits to the inputs of the processor,
wherein the intelligent multiplexer changes a number of the analog-to-digital conversion circuits connected to one first photon-counting detector of the plurality of photon-counting detectors based on the photon-counting rate.

2. The photon-counting apparatus according to claim 1, wherein the photon-counting apparatus is integrated into a computer-aided tomography (CT) system to capture data from the first photon-counting detectors.

3. The photon-counting apparatus according to claim 2, further comprising:
an X-ray tube; and
a reconstruction circuit configured to reconstruct CT images based on the digital photon-counting signals generated by the intelligent multiplexer.

4. The photon-counting apparatus according to claim 3, wherein the X-ray tube rotates around a patient table, and the first photon-counting detectors are located at fixed positions around the patient table.

5. The photon-counting apparatus according to claim 1, wherein the photon-counting rate is a number of photons impinging on the first photon-counting detectors during a predetermined time interval.

6. The photon-counting apparatus according to claim 1, wherein the intelligent multiplexer interleaves digital photon-counting signals of a subset of analog-to-digital conversion circuits when the photon-counting rate exceeds a first predetermined threshold.

7. The photon-counting apparatus according to claim 6, wherein the intelligent multiplexer interleaves digital photon-counting signals from two analog-to-digital conversion circuits when the photon-counting rate exceeds the first predetermined threshold.

8. The photon-counting apparatus according to claim 7, wherein the intelligent multiplexer interleaves digital photon-counting signals from three analog-to-digital conversions circuits when the photon-counting rate exceeds a second predetermined threshold that is higher than the first predetermined threshold.

9. The photon-counting apparatus according to claim 8, wherein the intelligent multiplexer interleaves digital photon-counting signals from four analog-to-digital conversion circuits when the photon-counting rate exceeds a third predetermined threshold that is higher than the second predetermined threshold.

10. The photon-counting apparatus according to claim 9, wherein the analog-to-digital conversion circuits switch to an energy integration mode when the photon-counting rate exceeds a fourth predetermined threshold that is higher than the third predetermined threshold.

11. The photon-counting apparatus according to claim 1, further comprising:
an energy integrating detector configured to integrate signals from second photon-counting detectors adjacent to the plurality of first photon-counting detectors in order to determine the photon-counting rate.

12. The photon-counting apparatus according to claim 1, further comprising:
second photon-counting detectors distributed among the plurality of first photon-counting detectors and configured to provide an indication of the photon-counting rate.

13. The photon-counting apparatus according to claim 1, further comprising:
a preamplifier circuit configured to condition the photon-counting signals from the plurality of first photon-counting detectors.

14. The photon-counting apparatus according to claim 13, wherein during an auto-adjust phase during which the preamplifier circuit is adjusted, the processor uses initial waveforms of the digital photon-counting signals to determine the photon-counting rate.

15. The photon-counting apparatus according to claim 14, wherein during the auto-adjust phase, the processor uses a difference between levels of the digital photon-counting signals and a predetermined baseline level to determine the photon-counting rate.

16. The photon-counting apparatus according to claim 1, wherein the intelligent multiplexer is implemented on a Field Programmable Gate Array (FPGA).

17. The photon-counting apparatus according to claim 10, further comprising:
an electronic memory circuit configured to store a look-up table associating different interconnection patterns between the plurality of first photon-counting detectors and the plurality of analog-to-digital conversion circuits with the first, second, third and fourth predetermined thresholds, the look-up table further associating different interleaving patterns of the digital photon-counting signals from the plurality of analog-to-digital conversion circuits with the first, second, third and fourth predetermined thresholds.

18. The photon-counting apparatus according to claim 10, wherein in the energy integration mode, each analog-to-digital conversion circuit converts a photon-counting signal to a digital photon-counting signal using oversampling and decimation.

19. A method for a photon-counting apparatus, comprising:
generating a plurality of photon-counting signals based on impingement of photons on a plurality of photon-counting detectors;
converting at least a subset of the plurality of photon-counting signals to digital photon-counting signals in a plurality of analog-to-digital conversion circuits;
determining a photon-count rate in a processor; and
causing an intelligent multiplexer, including a first portion configured to form connections from outputs of the first plurality of photon-counting detectors to inputs of the plurality of analog-to-digital conversion circuits and a second portion configured to form connections from outputs of the plurality of analog-to-digital conversion circuits to inputs of the processor, to modify the connections from the outputs of the plurality of photon-counting detectors and the inputs the plurality of analog-to-digital conversion circuits based on the photon-count rate, the intelligent multiplexer providing a set of digital photon-counting signals to the processor based on the connections from the outputs of the analog-to-digital conversion circuits to the inputs of the processor,
wherein a number of analog-to-digital conversion circuits connected to one first photon-counting detector of the plurality of photon-counting detectors is changed based on the photon-counting rate.

20. A non-transitory computer-readable medium encoded with computer-readable instructions thereon that, when executed by a computer, cause the computer to perform a method comprising:
generating a plurality of photon-counting signals based on impingement of photons on a plurality of photon-counting detectors;
converting at least a subset of the plurality of photon-counting signals to digital photon-counting signals in a plurality of analog-to-digital conversion circuits;
determining a photon-count rate in a processor; and
causing an intelligent multiplexer, including a first portion configured to form connections from outputs of the first plurality of photon-counting detectors to inputs of the plurality of analog-to-digital conversion circuits and a second portion configured to form connections from outputs of the plurality of analog-to-digital conversion circuits to inputs of the processor, to modify the connections from the outputs of the plurality of photon-counting detectors to the plurality of analog-to-digital conversion circuits based on the photon-count rate, the intelligent multiplexer providing a set of digital photon-counting signals to the processor based on the connections from the outputs of the analog-to-digital conversion circuits to the inputs of the processor,
wherein a number of analog-to-digital conversion circuits connected to one first photon-counting detector of the plurality of photon-counting detectors is changed based on the photon-counting rate.

* * * * *